(12) United States Patent
García Fábrega et al.

(10) Patent No.: US 8,463,114 B2
(45) Date of Patent: Jun. 11, 2013

(54) MOTION-SENSING EVAPORATOR DEVICE FOR VOLATILE SUBSTANCES

(75) Inventors: Rubén García Fábrega, Barcelona (ES); David Moreno Pérez, Barcelona (ES); Jose Antonio Muñoz Martínez, Barcelona (ES); Joan Gusi Hidalgo, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 496 days.

(21) Appl. No.: 12/672,343

(22) PCT Filed: Aug. 24, 2007

(86) PCT No.: PCT/EP2007/058816
§ 371 (c)(1),
(2), (4) Date: Jun. 23, 2010

(87) PCT Pub. No.: WO2009/018862
PCT Pub. Date: Feb. 12, 2009

(65) Prior Publication Data
US 2010/0266266 A1 Oct. 21, 2010

(30) Foreign Application Priority Data
Aug. 7, 2007 (ES) .................................. 200702226

(51) Int. Cl.
*F24F 6/08* (2006.01)
*H05B 3/06* (2006.01)
(52) U.S. Cl.
USPC ........... 392/395; 392/397; 392/390; 392/392; 392/394; 392/398; 219/521; 219/522

(58) Field of Classification Search
USPC ......... 392/395, 390, 392, 394, 386, 397–398; 219/521, 522
See application file for complete search history.

(56) References Cited

U.S. PATENT DOCUMENTS

| 5,071,621 A | 12/1991 | Tokuhiro et al. .................. 422/4 |
| 6,766,817 B2 | 7/2004 | da Silva .............................. 137/1 |
| 7,285,255 B2 | 10/2007 | Kadlec et al. ................. 422/305 |

FOREIGN PATENT DOCUMENTS

| CN | 1700932 | | 11/2005 |
| DE | 10 2005 041986 A1 | | 3/2007 |
| DE | 102005041986 | * | 3/2007 |
| EP | 0 325 468 A | | 7/1989 |
| EP | 0325468 | * | 7/1989 |
| GB | 2 227 665 A | | 8/1990 |
| GB | 2227665 | * | 8/1990 |

OTHER PUBLICATIONS

Chinese Office Action dated Mar. 2, 2011 with English translation.
International Search Report dated Apr. 11, 2008, issued in corresponding international application No. PCT/EP2007/058816.
E-mail dated Oct. 22, 2010 from Elson Silva, Ph.D. regarding "Respecting Hydrology Science in the Patenting System".

* cited by examiner

*Primary Examiner* — Shawntina Fuqua
(74) *Attorney, Agent, or Firm* — Ostrolenk Faber LLP (57) ABSTRACT

The present invention relates to an evaporator device for volatile substances, preferably usable in vehicles, which is activated by the movement of the device, whereby the device will begin to evaporate a volatile substance when the user is in the vehicle. The device comprises a casing, a diffuser, and at least one movement sensor, the diffuser being operable by the sensor.

10 Claims, 7 Drawing Sheets

MOTION-SENSING EVAPORATOR DEVICE FOR VOLATILE SUBSTANCES

CROSS REFERENCE TO RELATED APPLICATIONS

The present application is a 35 U.S.C. §371 National Phase conversion of PCT/EP2007/058816, filed Aug. 24, 2007, which claims benefit of Spanish Application No. P200702226, filed Aug. 7, 2007, the disclosure of which is incorporated herein by reference. The PCT International Application was published in the English language.

OBJECT OF THE INVENTION

The present invention refers in general to evaporator devices for volatile substances for closed spaces.

In more specific terms, the invention relates to an evaporator device for volatile substances, preferably for vehicles, which is activated by means of the movement of the actual device, the object being to guarantee that the device only evaporates the volatile substance when the vehicle is in use or occupied.

BACKGROUND OF THE INVENTION

There are many types of evaporation devices for volatile substances, generally air-fresheners and/or insecticides, which utilise a wick, a spray, a permeable membrane, gel or impregnated paper as the medium for the evaporation of said substance.

These appliances need means which allow their activation by the user, and in some applications means for the automatic activation or deactivation, for which reason they employ light sensors to select different uses of the device during the day and at night, or to activate the evaporator for example when the user is present.

In certain applications like for example for the diffusion of a volatile substance inside a vehicle, the known sensor-equipped devices do not offer satisfactory benefits, since they do not only detect the presence of movement or luminous conditions inside the vehicle, but are also sensitive to movements or light conditions outside the vehicle, for example a person passing on foot near the vehicle.

Thus the known devices with automatic operation are not appropriate for their use in a vehicle in that the mere proximity of a person to the vehicle can initiate the evaporation of the substance, producing an unnecessary waste thereof and an unpleasant aromatic saturation inside the vehicle.

DESCRIPTION OF THE INVENTION

An aspect of the invention relates to an evaporator device for volatile substances which comprises a casing and means for the diffusion of an active substance supported by said casing. The device is characterized in that it comprises at least a movement sensor of said casing, whereby said diffusion means are operable by means of said sensor, in such a way that the diffusion means are put into operation or the effect thereof is enhanced, either by means of increasing the speed of a fan, raising the temperature of a heater, a change in the frequency of pulses, or in the activation of some secondary means of diffusion.

The movement sensor is integral with the casing and detects the movement of the appliance or of the device, not the movement of an object which is moving close to the same, whereby it is guaranteed that the diffusion of the volatile substance takes place only when the user is in the vehicle, therefore saving unnecessary consumption of the same and avoiding saturating the interior of the vehicle.

DESCRIPTION OF THE DRAWINGS

To supplement the description that is being made and with the object of assisting in a better understanding of the characteristics of the invention, in accordance with a preferred example of practical embodiment thereof, attached as an integral part of said description, is a set of drawings wherein by way of illustration and not restrictively, the following has been represented.

PREFERRED EMBODIMENT OF THE INVENTION

In a preferred embodiment the diffusion means consists of a fan, and the volatile substance situated in a cartridge equipped with permeable membrane. Some programmable electronic means control the activation of the diffusion elements, in this case the fan, taking into consideration the detection of the movement sensor.

Thus, when a user enters his car and puts it in movement, the movement sensor will detect the movement of the vehicle and in turn the electronic means connected to the sensor, will act on the fan, either to make it work or to increase its speed.

The electronic means can be programmed to maintain the fan in operation during a period of time or to allow the operation thereof during preset cycles of time or as selected by the user.

The fan is activated by means of batteries, for that the device also has indication means that are activated when the battery charge is consumed, like an LED diode for example which lights or flashes in such an eventuality.

When the vehicle moves, the movement sensor detects such circumstance and the electronic means associated with the sensor are activated in response to said detection and produces an electric signal to act on the diffusion means to allow, start or enhance the evaporation of the volatile substance.

The movement or vibration sensor can consist for example of an accelerometer.

The electronic means are programmed to maintain the activation state of the diffusion means during a certain time, after which if the movement sensor has ceased to detect the movement of the vehicle, it disconnects the diffusion elements.

The volatile substance can be held in any known type of container, like a container for example with permeable membrane, or a bottle with a wick partially immersed therein. The diffusion means can also be of any known type, like for example heater elements, fan, spray with solenoid-valve, piezoelectric mist generator, etc. The casing can have means that prevent contact with the membrane or wick.

The casing is provided with means that allow its fastening on any internal surface of a vehicle, like the interior part of a door, the sunshade or a seat for example.

Figure 1:
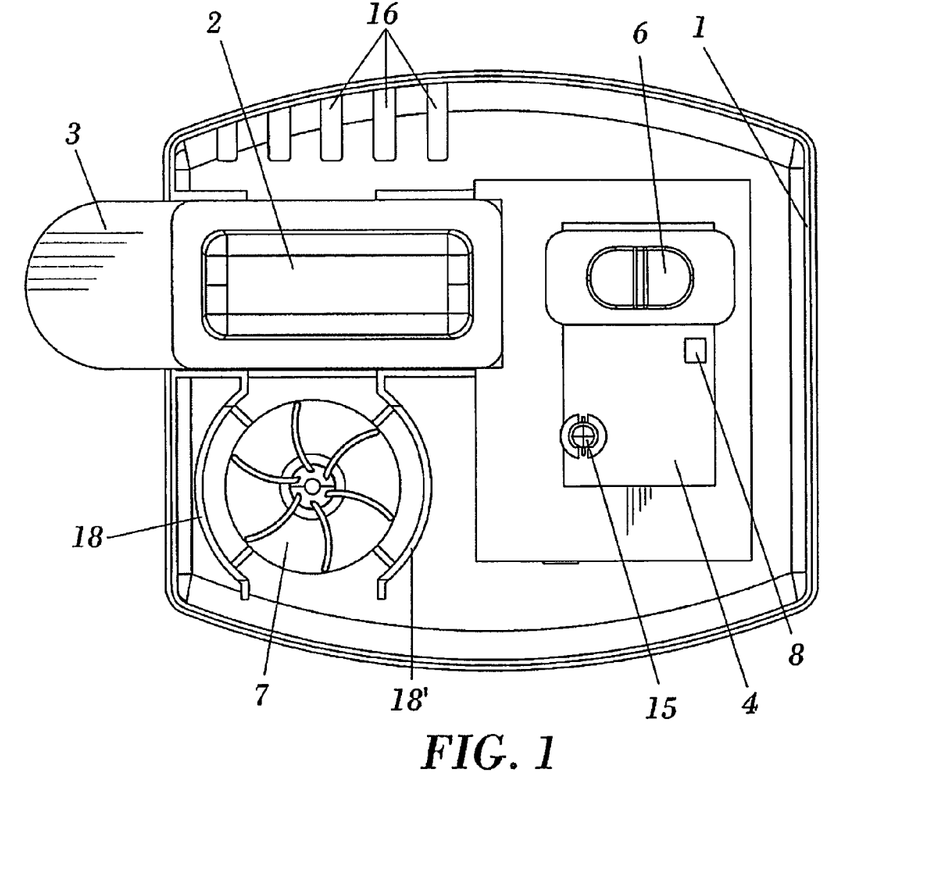
FIG. 1.—It shows a plan view of a preferred embodiment of an evaporator device according to the invention, where the upper part of the casing has not been represented to allow visualization of its interior.
Figure 2:
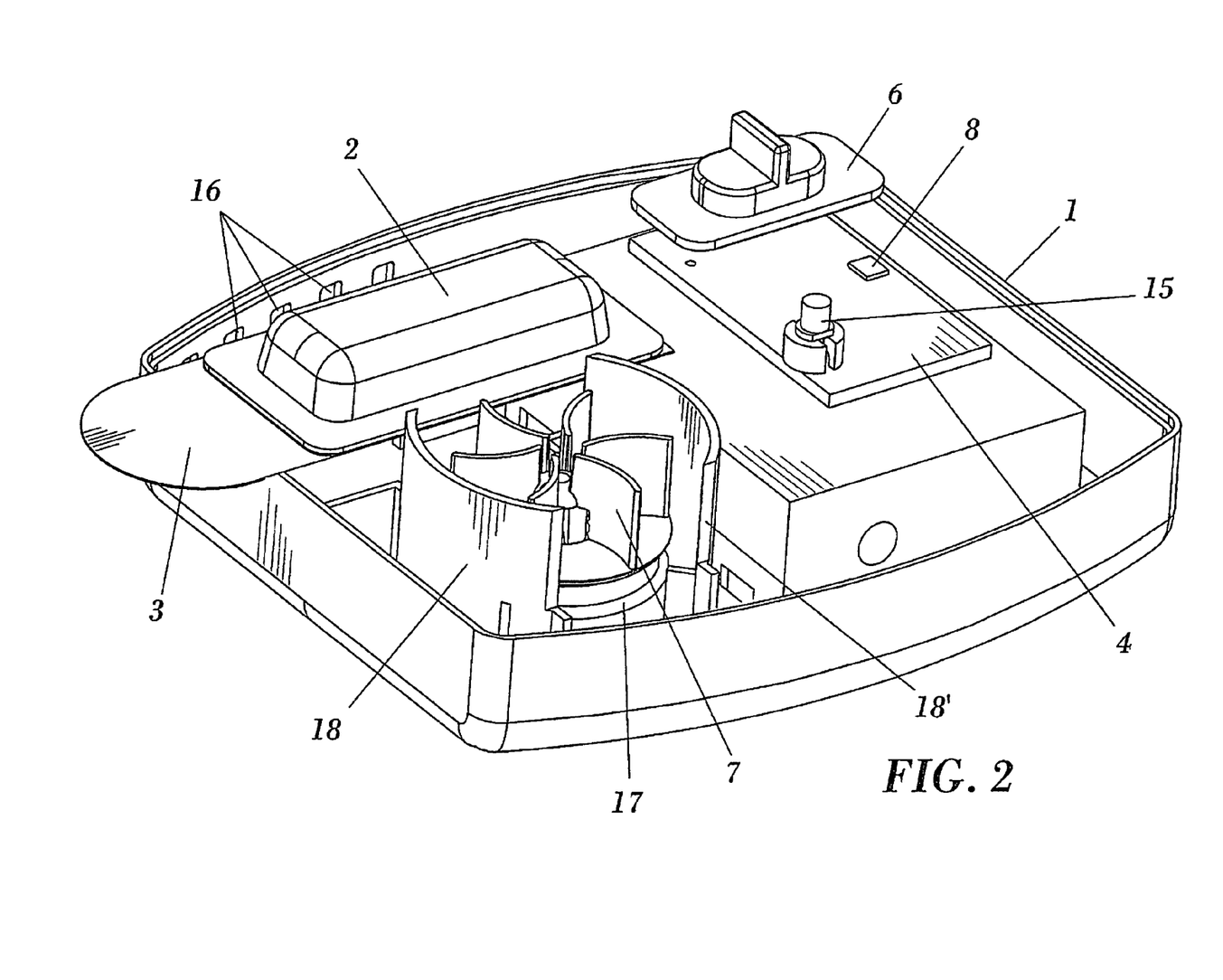
FIG. 2.—It shows a perspective view of the device of FIG. 1.

In FIG. 1 a preferred embodiment of the invention is shown, wherein a casing (1) of the device houses a container (2) of the volatile substance equipped with a membrane (not represented) to allow its evaporation. A film (3) covers said membrane during the storage and transport of the product to avoid the undesired evaporation of the substance.

The electronic means are mounted on a printed circuit board (4), which is powered by means of some batteries (5), for example button batteries or conventional batteries. A switch (6) allows the user to connect or disconnect the device.

In this preferred embodiment, the diffusion means consist of a fan (7) arranged to blow air onto said membrane and activate or begin the evaporation of the volatile substance, governed by the electronic means which in turn are activated by the movement sensor (8). A light-emitting diode or LED (15) indicates the operational state of the device.

Figure 3:
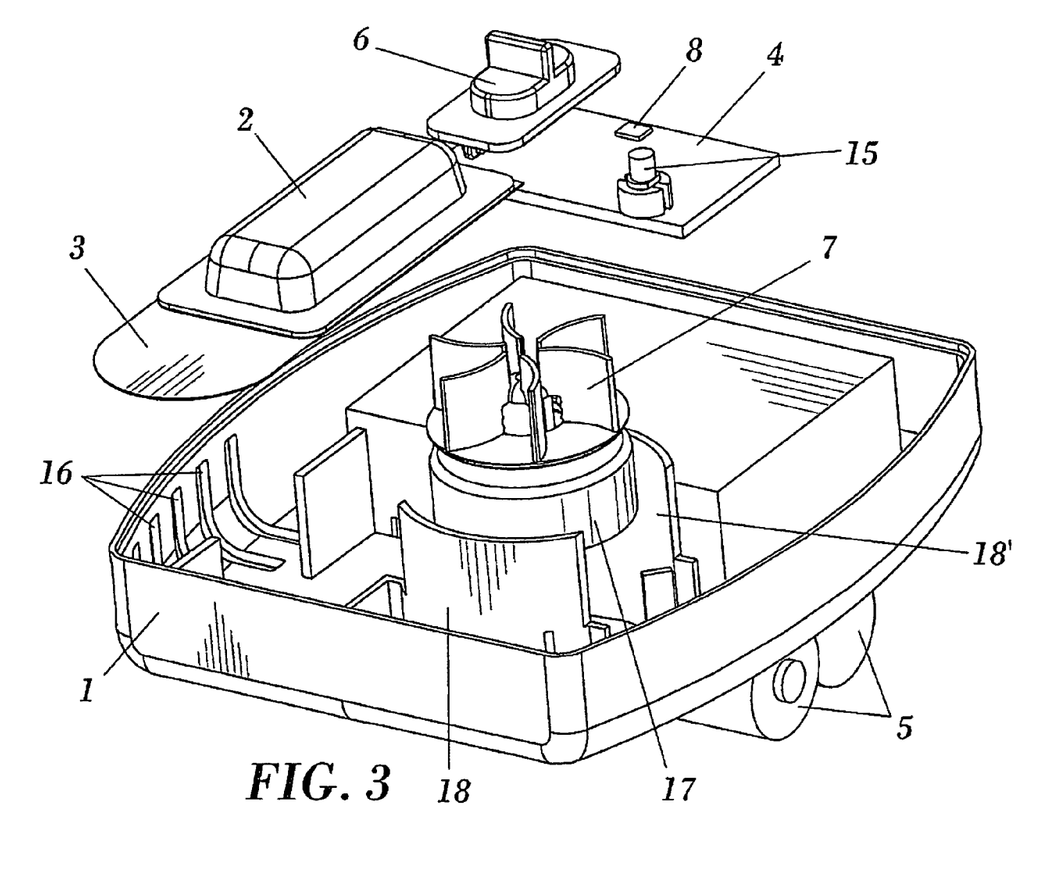
FIG. 3.—It shows another perspective view and in exploded form of the same device.
Figure 4:
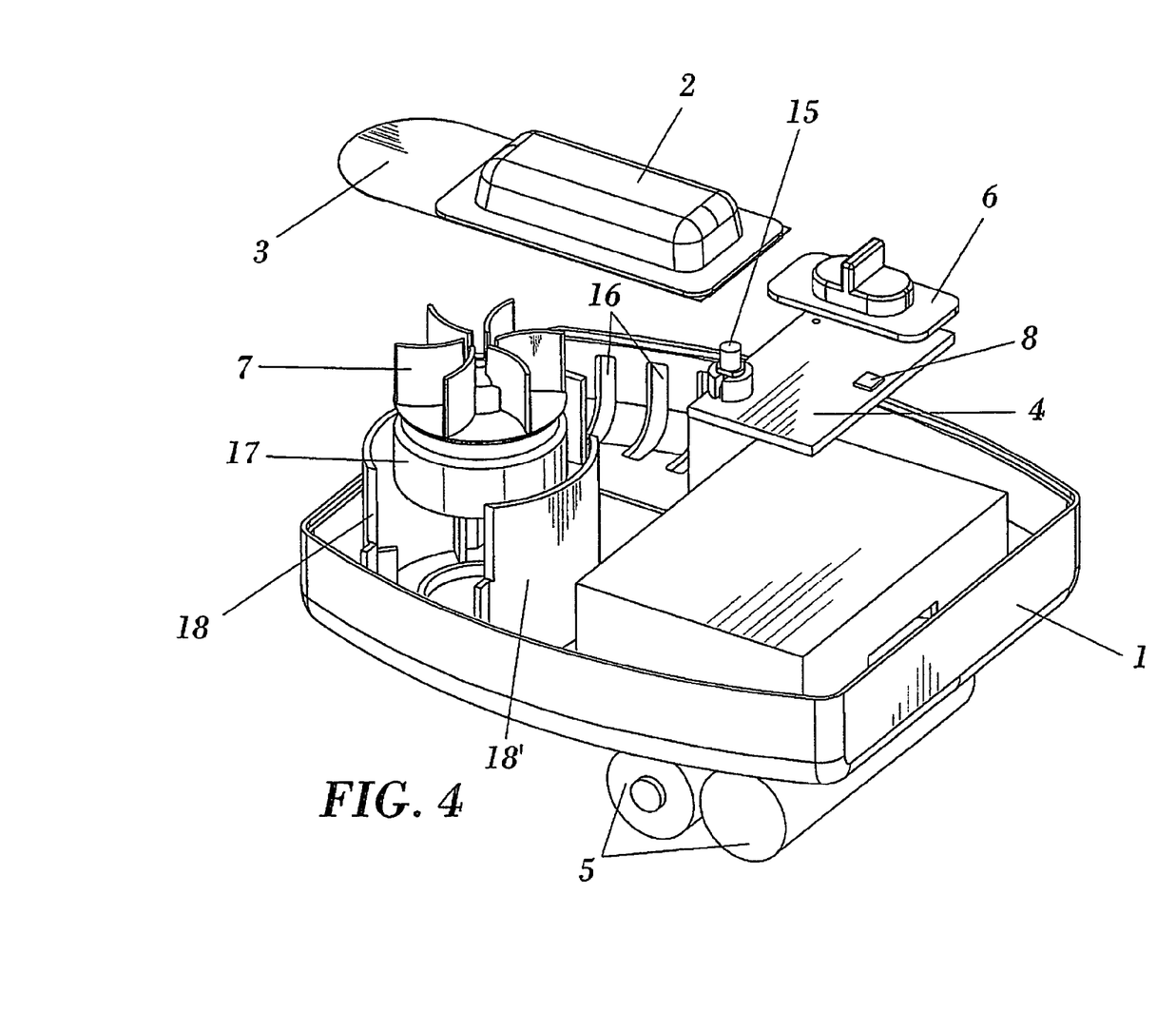
FIG. 4.—It shows another view in perspective and In exploded form of the same device.

Especially in FIG. 3 the openings (16) are observed arranged on one end of the casing (1) to allow the egress of the air current with evaporated product driven by the fan (7).

The fan (7) is operated by a direct current motor (17), and in its mounting inside the casing (1) it is situated between two (18, 18') deflecting baffles which have an arched shaped and are arranged so that they direct the air flow driven by the fan toward the bottom part of the container (2).

Figure 5:
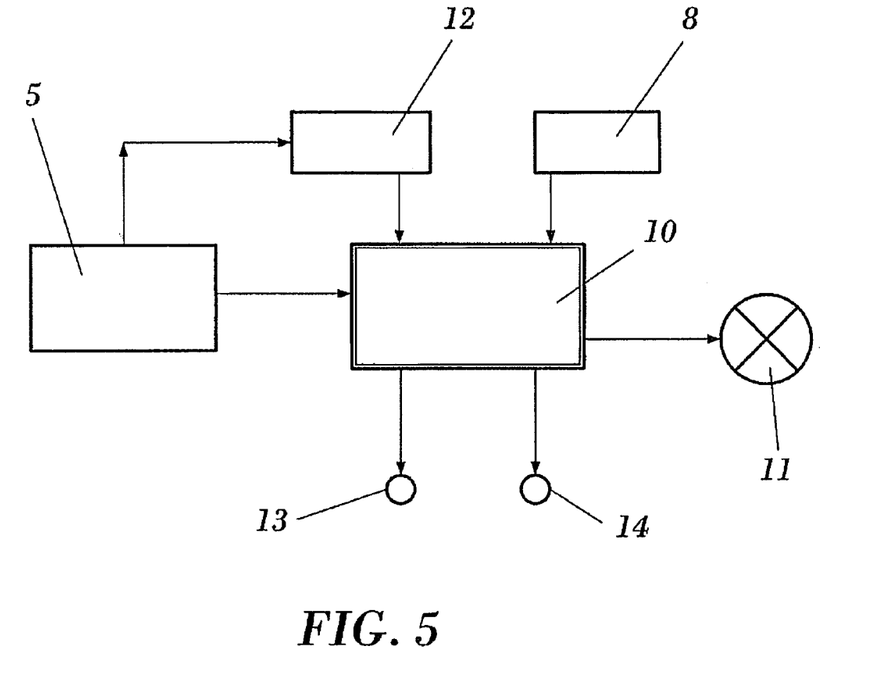
FIG. 5.—It shows an electrical schematic of this device.

In FIG. 5 the electrical schematic of the device is shown, wherein the electronic means are implemented by a microcontroller (10) which receives as inputs the signal from the movement sensor (8) and from a battery-low indicator (12). As outputs this microcontroller (10) has the motor (11) of the fan, a light-emitting indicator (13) of the operational state of the device, and a battery-low indicator (14).

The batteries (5) feed the microcontroller and the battery-low detector (12).

Figure 6:
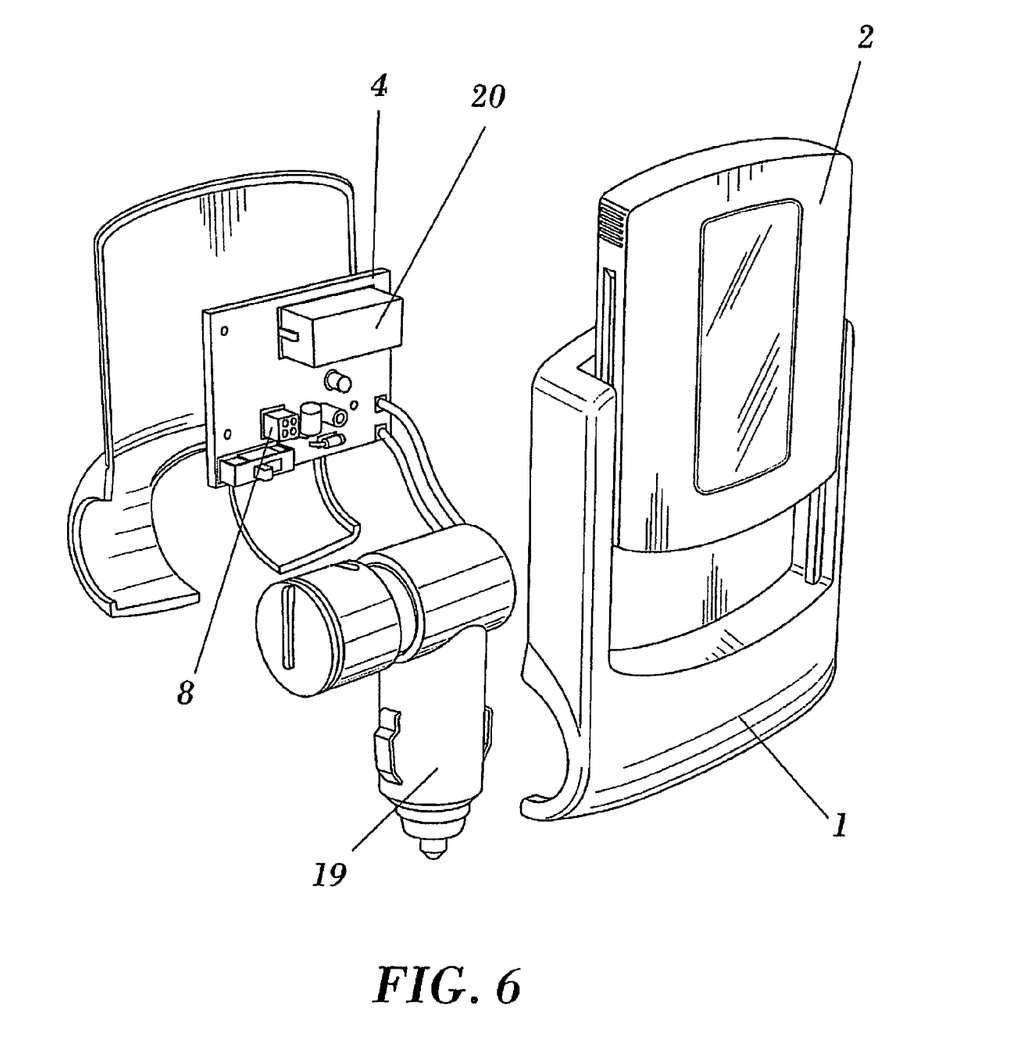
FIG. 6.—It shows a view in perspective and in exploded form of another embodiment of the invention.
Figure 7:
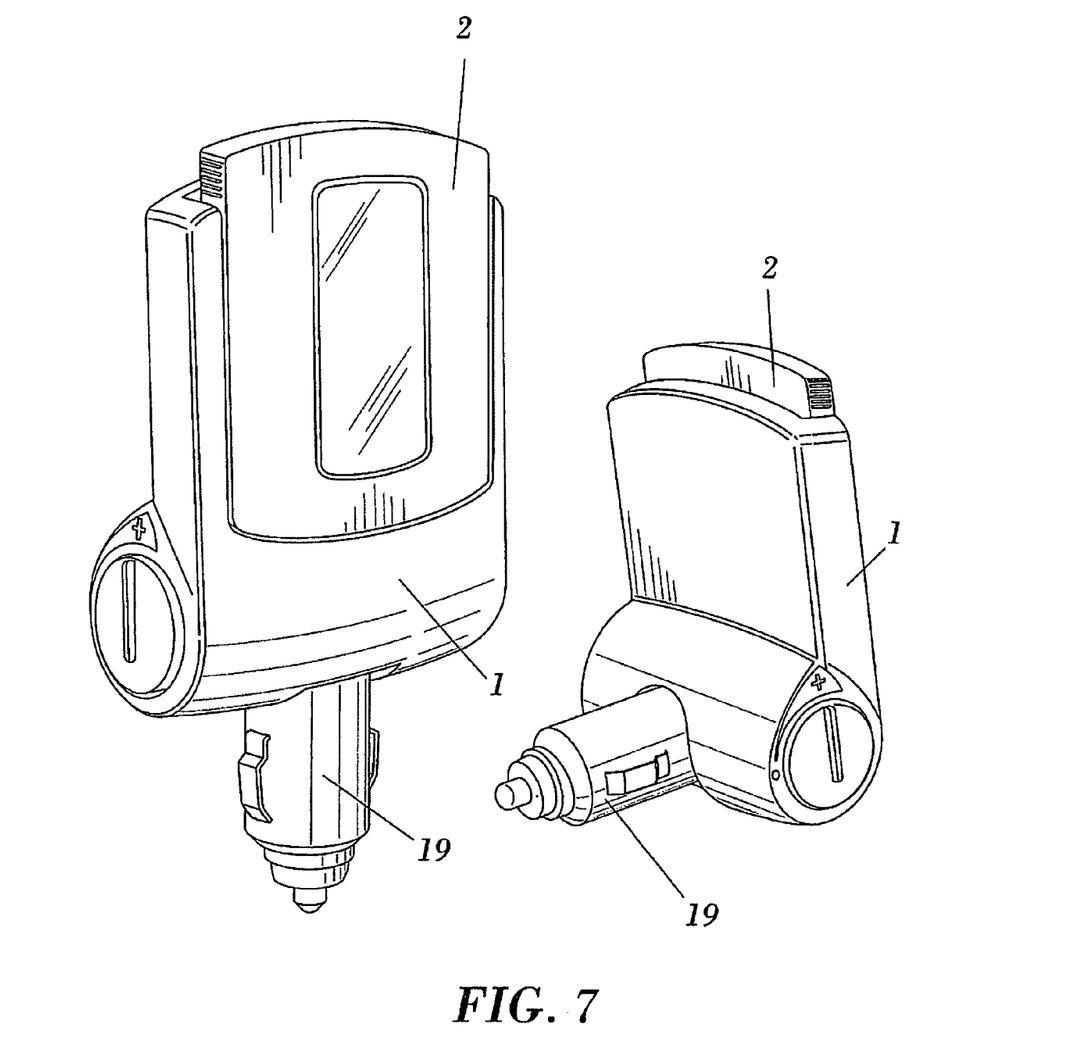
FIG. 7.—It shows individual views in perspective of the device of FIG. 6 in the closed position.

In the embodiment of FIG. 6, the power supply of the device has been implemented by means of an electric connector (19) to be plugged into the electric outlet conventionally present in a saloon type car, so the device can be used in this type of vehicle. Instead of a fan there is a heater element (20), dependent upon the electronic means as described for the preceding embodiment.

The container (2) of the volatile substance can be any type of known container, like for example a container with permeable membrane.

Diverse possibilities of practical embodiments of the invention are described in the dependent claims enclosed.

What is claimed is:

1. An evaporator device for volatile substances comprising:
   a casing configured to support a volatile substance;
   an electrically powered diffuser provided in said casing for the diffusion of said volatile substance;
   at least one movement sensor arranged to detect the movement of said casing;
   a source of electric power to power said diffuser; and
   an electronic controller associated with said movement sensor, with said source of electric power and with said diffuser;
   wherein said electronic controller is configured to operate said diffuser responsive to the detection of movement of said casing by said sensor.

2. A device according to claim 1, wherein said diffuser is arranged to activate the evaporation of said substances, and selected from a group consisting of i) a fan, ii) heating resistances, iii) means for concealment of said membrane or wick which are closed or opened over the membrane or wick, iv) spray with solenoid valve, v) mist generator, and vi) any combination of the foregoing.

3. A device according to claim 1, wherein said movement sensor is selected from a group consisting of an accelerometer, a vibration sensor, an omnidirectional vibration sensor, a movement sensor, an inclination sensor, an angle sensor, and a position sensor.

4. A device according to claim 1, further comprising a volatile substance container provided with a wick or a permeable membrane to evaporate said substance.

5. A device according to claim 1, wherein said source of electric power comprises a battery or an electric connector.

6. A device according to claim 1, wherein said electronic controller is programmed to activate said diffuser in preset periods of time.

7. A device according to claim 1, wherein said movement sensor causes the activation of said diffuser.

8. A device according to claim 1, wherein said movement sensor causes the enhancement of the effect of said diffuser.

9. A device according to claim 1, wherein said casing further comprises a fastener for fastening thereof on an interior surface of a vehicle.

10. A device according to claim 1, wherein said electronic controller and said movement sensor reside in said casing.

* * * * *

UNITED STATES PATENT AND TRADEMARK OFFICE
CERTIFICATE OF CORRECTION

PATENT NO.        : 8,463,114 B2
APPLICATION NO.   : 12/672343
DATED             : June 11, 2013
INVENTOR(S)       : García Fábrega et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 629 days.

Signed and Sealed this
Eighth Day of September, 2015

Michelle K. Lee
*Director of the United States Patent and Trademark Office*